(12) United States Patent
Vashi

(10) Patent No.: US 6,247,923 B1
(45) Date of Patent: Jun. 19, 2001

(54) SELF-LOCKING ORTHODONTIC BRACKET

(76) Inventor: Nikhil Shankarlal Vashi, Neelkamth, 15-A Unik Society Model Town J.P. Road, Andheri (W), Mumbai, Maharashtsa (IN), 400 053

( * ) Notice: Subject to any disclaimer, the term of this patent is extended or adjusted under 35 U.S.C. 154(b) by 0 days.

(21) Appl. No.: 09/576,934

(22) Filed: May 24, 2000

(51) Int. Cl.[7] ..................................... A61C 3/00
(52) U.S. Cl. .............................. 433/10; 433/11
(58) Field of Search ................. 433/8, 10, 11, 433/13, 14

(56) References Cited

U.S. PATENT DOCUMENTS

| | | |
|---|---|---|
| 2,671,964 | 3/1954 | Russel et al. . |
| 3,131,474 | 5/1964 | Johnson . |
| 3,780,437 | 12/1973 | Wildman . |
| 4,023,274 | 5/1977 | Wallshein . |
| 4,268,249 | 5/1981 | Forster . |
| 4,492,573 * | 1/1985 | Hanson ................. 433/11 |
| 4,559,012 | 12/1985 | Pletcher . |
| 4,561,844 | 12/1985 | Bates . |
| 4,634,662 | 1/1987 | Rosenberg . |
| 5,094,614 | 3/1992 | Wildman . |
| 5,125,832 | 6/1992 | Kesling . |
| 5,322,435 | 6/1994 | Pletcher . |
| 5,466,151 | 11/1995 | Damon . |
| 5,618,176 * | 4/1997 | Andreiko et al. ................. 433/11 |
| 5,711,666 | 1/1998 | Hanson . |
| 5,738,513 | 4/1998 | Hermann . |
| 5,857,849 | 1/1999 | Kurz . |
| 5,906,486 | 5/1999 | Hanson . |
| 5,908,293 | 6/1999 | Voudouris . |
| 5,913,680 | 6/1999 | Voudouris . |
| 5,967,773 | 10/1999 | Roman . |
| 5,971,753 | 10/1999 | Herser . |

* cited by examiner

Primary Examiner—Nicholas D. Lucchesi

(57) ABSTRACT

A self-locking orthodontic bracket comprises a body (1) and a base (2) contoured to fit a tooth surface. The body (1) has an arch wire slot (3) extending horizontally across the labial/buccal surface, a pair of tie wings (4A and 4B) projecting vertically on either side of the arch wire slot (3), a retainer member (6) having a transverse part and two perpendicular horizontal extensions at the end (6A and 6B) attached to the sides of one of the tie wings (4A) and a slidable cover (5) retained and guided in the recess created between the retainer member (6) and the surface of the tie wing (4A). The slidable cover (5) can be moved vertically towards the tip of the tie wing (4A) to open the arch wire slot (3) and it can be moved in the opposite direction to close the arch wire slot (3).

Different embodiments of the slidable cover (5) and the retainer member (6) are disclosed herein.

42 Claims, 14 Drawing Sheets

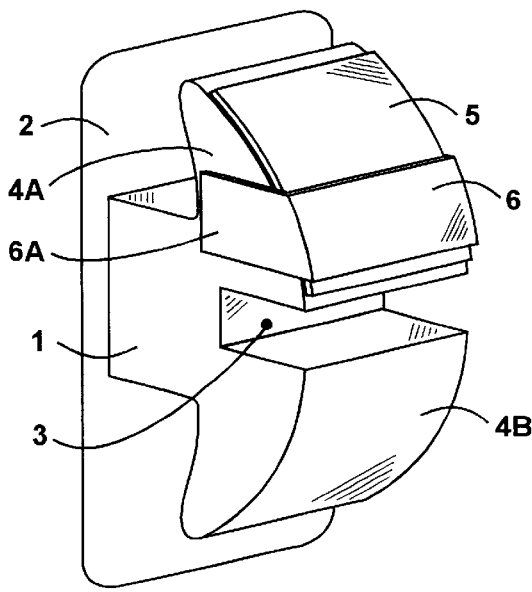
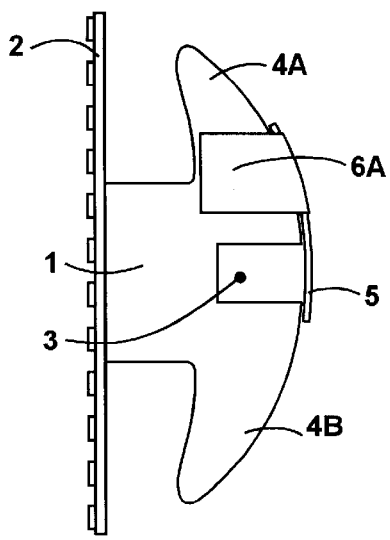
Fig. 5
Fig. 6
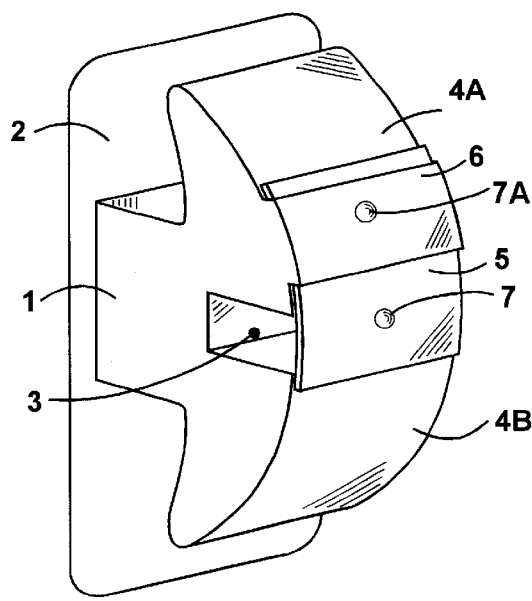
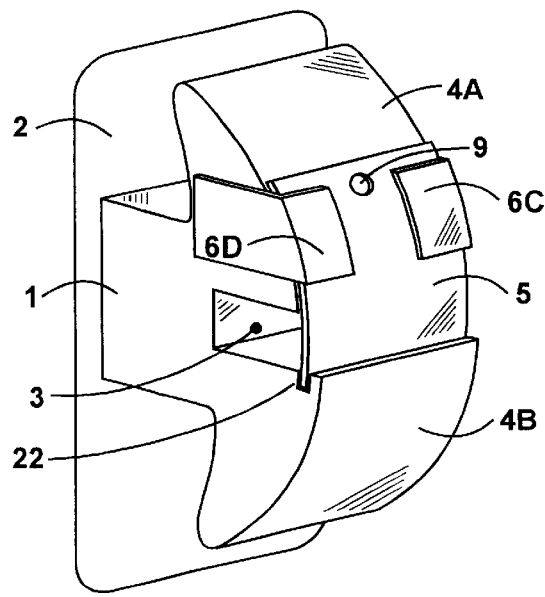
Fig. 7
Fig. 8

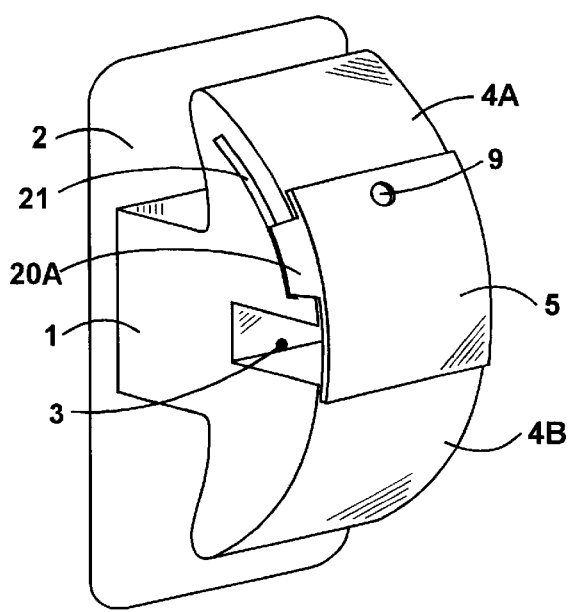
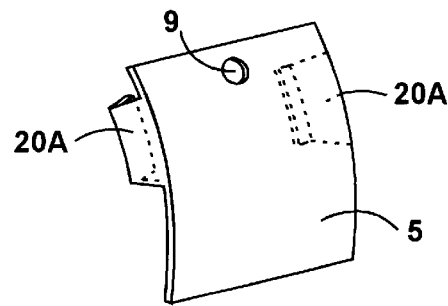
Fig. 16A
Fig. 16B
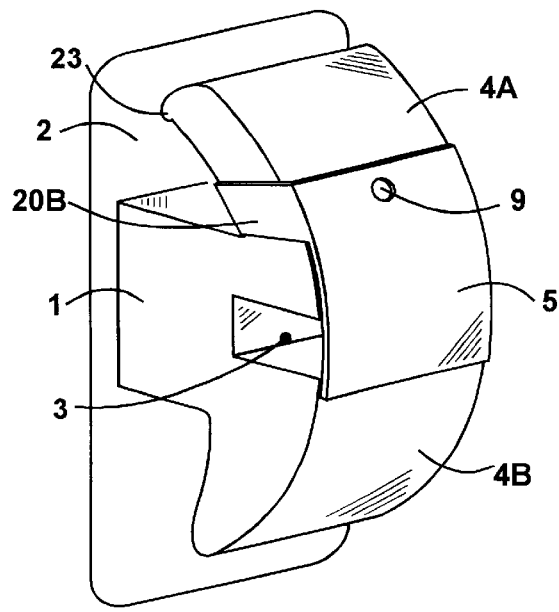
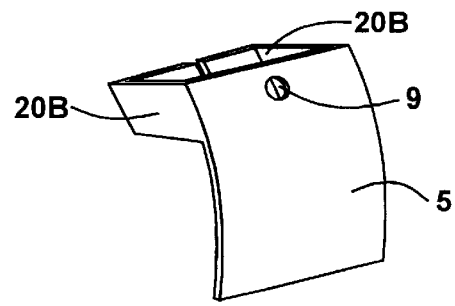
Fig. 17A
Fig. 17B

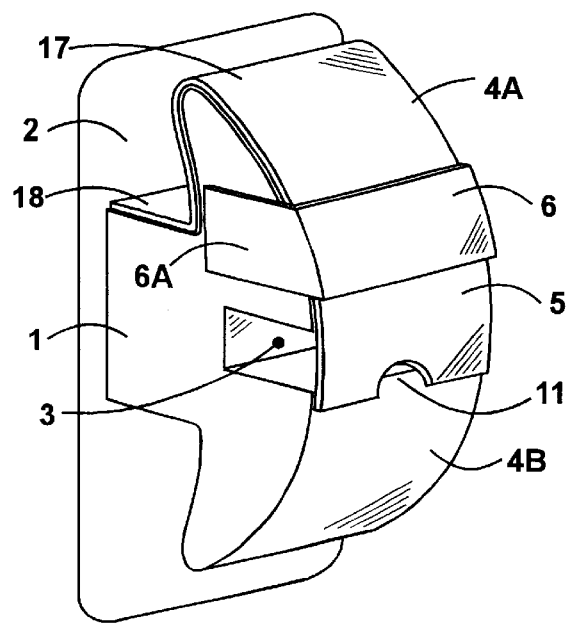
Fig. 18A
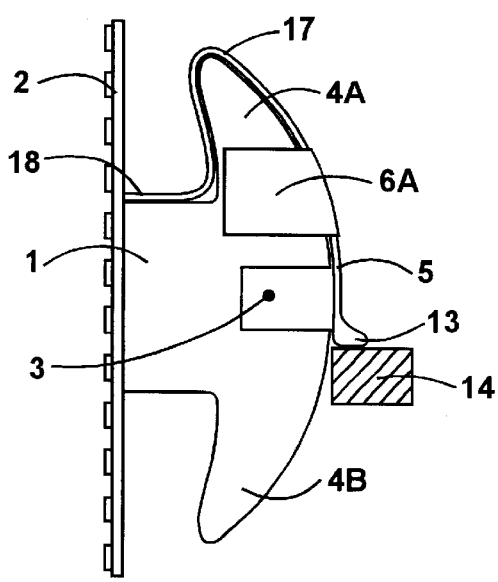 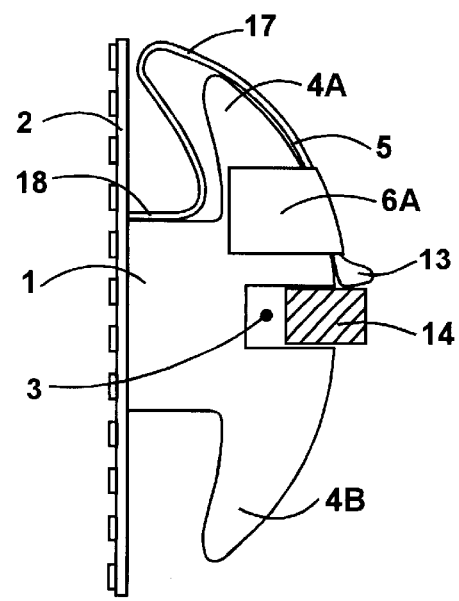
Fig. 18B　　　　　　　　Fig. 18C

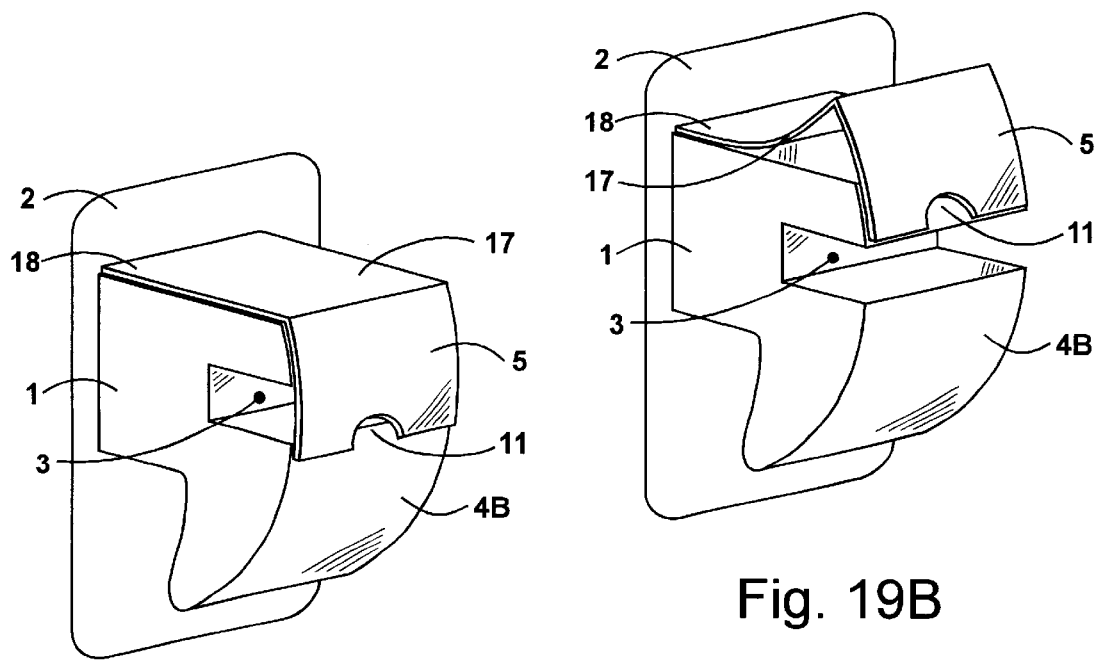
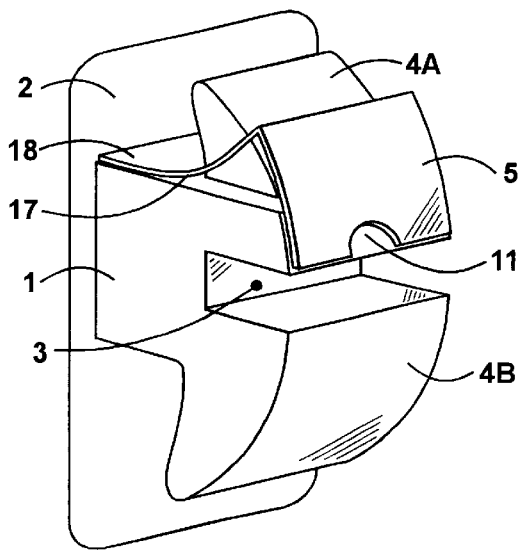
Fig. 19A
Fig. 19B
Fig. 19C
Fig. 19D

SELF-LOCKING ORTHODONTIC BRACKET

FIELD OF THE INVENTION

This invention relates to self-locking or ligatureless orthodontic brackets.

BACKGROUND OF THE INVENTION

Orthodontic brackets may be used with arch wires to straighten irregular teeth. These brackets are attached to the teeth and engage a flexible arch wire that exerts pressure upon them to move the teeth. The most commonly used brackets are edgewise brackets as shown in FIGS. 1, 2, and 3. FIG. 1 shows a Siamese twin bracket, FIG. 2 shows a single bracket with rotation wings, and FIG. 3 shows a modified edgewise bracket known as Tip-Edge bracket. Such brackets typically include an arch wire slot that extends horizontally across the face of the bracket for the reception of the arch wire. This slot can be angularly oriented to minimize bending of arch wires. A pair of wings extend vertically on either side of the arch wire slot from the bracket enabling ligature means to be tied to the bracket to retain the arch wire in the slot. Stainless steel ligature ties or elastomeric ligature rings are conventionally used as the ligature means.

Placement of these small wires or elastomeric ligature rings requires considerable time during initial installation of an arch wire. It is also normally necessary to remove and replace the ligatures each time an arch wire is changed.

Ligatures also tend to make proper oral hygiene more difficult as the wires can trap food particles, and the twisted ends of a ligature may be shifted during cleaning into a position where irritation of the patient's gums or cheek tissues occurs.

When repositioning teeth with brackets, it is often necessary to cause the teeth and the brackets to slide along the arch wire. Since the ligature ties are in firm contact with the arch wire, friction is generated between the brackets and the arch wire affecting the tooth movements adversely.

Many of these problems presented by ligatures are overcome by self-locking orthodontic brackets. So far numerous attempts have been made to develop such brackets.

U.S. Pat. No. 2,671,964 to Russel et al. that was issued on Mar. 16, 1954 shows a hollow bracket with a slidable cover within. This bracket does not have tie wings that are necessary for engaging elastomeric chains and continuous ligature ties. U.S. Pat. No. 3,131,474 to Johnson also shows a hollow bracket with a slidable cover recessed with in. Both these brackets are hollow and have to be manufactured from metal sheets whereas the contemporary brackets are solid.

U.S. Pat. No. 5,094,614 to Wildman issued on Mar. 10, 1992 discloses a slidable closure that engages the front of the arch wire. The closure is recessed from the front or anterior surface of the disclosed bracket.

U.S. Pat. Nos. 5,275,557; 5,429,500, & 5,466,151 to Damon show a slidable cover supported by sliding guides that engage the opposed side surfaces of tying lugs. A transverse flat spring is recessed within the fixed wall to selectively engage indented areas on the posterior surface of the cover and serve as detent.

Another slidable cover has been disclosed in U.S. Pat. No. 5,322,435 issued to Pletcher on Jun. 21, 1994. A resilient member is provided to retain the slide member of the bracket in either the open or closed position, while preventing excessive sliding movement that could disengage the slide member.

Various other locking means such as a slidable spring cover, a hinged locking cover, a rotary slidable cover, a bail type rotatable cover etc. have been disclosed in different U.S. Patents. "Activa" produced by A Company, "Speed" and "Edgelock" produced by Ormco Corporation, and others are typical examples of ligature-less brackets that are commercially available.

Of all these different locking means a sliding closure is particularly desirable because it can be easily manipulated and it reduce the time required for opening and closing of the arch wire slot during periodic adjustments of the arch wire. It also provides more precise control of the arch wire:. The other means are more complex, however, and therefore difficult and expensive to manufacture Also, they are not as compact as would be desired. Additionally, it is difficult to use auxiliary attachments with brackets without tie wings. Also, with brackets having detachable parts, there are chances of such parts getting separated accidentally and getting lost or swallowed by patients. Moreover, springs used as locking means are not strong enough to hold the arch wire into the slot.

OBJECTS AND ADVANTAGES

The object of the present invention is to provide a locking device for an orthodontic bracket that operates on the face of the bracket for opening and closing the arch wire slot. This is possible by means of the self-locking bracket and its different embodiments as described in this specification.

Accordingly, several objects and advantages of the present invention are:

1. to provide a self-locking or ligatureless orthodontic bracket that is easy to use,
2. to provide a self-locking or ligatureless orthodontic bracket that helps in reducing the time taken during insertion and removal of an arch wire,
3. to provide a self-locking or ligatureless orthodontic bracket that is easy to fabricate thereby making it less expensive,
4. to provide a self-locking or ligatureless orthodontic bracket that facilitates the use of auxiliary attachments by means of tie wings,
5. to provide a self-locking or ligatureless orthodontic bracket that considerably reduces the friction caused by the tying of ligature means to retain an arch wire into the arch wire slot, thereby facilitating tooth movements.
6. to provide a self-locking or ligatureless orthodontic bracket wherein the arch wire slot is closed automatically by a cover on releasing the pressure applied to the cover to open the slot.

SUMMARY OF THE INVENTION

This invention relates to a locking mechanism for securing an arch wire to an orthodontic bracket slot. This means is very easy to manufacture and easy to operate for closing and opening the arch wire slot. It eliminates the need for ligature wires and elastic ligatures, while keeping the tie wings intact for auxiliaries like power chains and continuous ligature ties.

The bracket of this invention has several novel aspects. In general, the bracket includes a bracket body attached to a base that is contoured to fit a tooth surface. The body of the bracket has an arch wire slot extending horizontally across the labial/buccal surface. In the preferred embodiment, at least one tie wig extends out vertically from the body. A retainer member having a transverse part and two perpendicular horizontal extensions at the end is attached to the sides of the tie wing. A slidable cover is retained and guided in the passageway created between the retainer member and the surface of the tie wing. The slidable cover can be moved vertically towards the tip of the tie wing to open the arch wire slot and it can be moved in the opposite direction to close the arch wire slot after the engagement of an arch wire into the slot. The cover fits closely in the passageway and is frictionally retained.

Various different embodiments of the bracket, the cover, and the retainer member are described which facilitate movements of the slidable cover and prevent inadvertent dislodgment of the cover from the bracket.

Although many different embodiments of the cover and the retainer member are disclosed in the specification, the cover works in the same manner in all the embodiments, i.e. by sliding over the face of the bracket. The difference lies only in the manner in which the slidable cover is retained on the face of the bracket and is guided to open and close the arch wire slot.

The objects and advantages of the present invention will become apparent from a consideration of the drawings and ensuing description.

DESCRIPTION OF DRAWINGS

FIG. 5 is a perspective view of the bracket shown in FIG. 4A showing the slidable cover in open position.

FIG. 6 is a side view of the orthodontic bracket of FIG. 4A.

FIG. 7 is a perspective view of another embodiment of an orthodontic bracket according to the present invention.

FIG. 8 is a perspective view of another embodiment of an orthodontic bracket according to the present invention.

FIG. 16A is a perspective view of another embodiment of an orthodontic bracket according to the present invention.

FIG. 16B is a perspective view of the slidable cover of FIG. 16A.

FIG. 17A is a perspective view of another embodiment of an orthodontic bracket according to the present invention.

FIG. 17B is a perspective view of the slidable cover of FIG. 17A.

FIG. 18A is a perspective view of another embodiment of an orthodontic bracket according to the present invention.

FIG. 18B is a side view of another embodiment of an orthodontic bracket according to the present invention showing a slidable cover in closed position.

FIG. 18C is a side view of the orthodontic bracket of FIG. 18B showing the slidable cover in open position.

FIG. 19A is a perspective view of another embodiment of an orthodontic bracket according to the present invention showing a slidable cover in closed position.

FIG. 19B is a perspective view of the orthodontic bracket of FIG. 19A showing the slidable cover in open position.

FIG. 19C is a perspective view of another embodiment of an orthodontic bracket according to the present invention showing a slidable cover in closed position.

FIG. 19D is a perspective view of the orthodontic bracket of FIG. 19C showing the slidable cover in open position.

DESCRIPTION OF THE INVENTION

The following describes the embodiments of present invention as illustrated in FIGS. 4A to 32.

Figure 1:
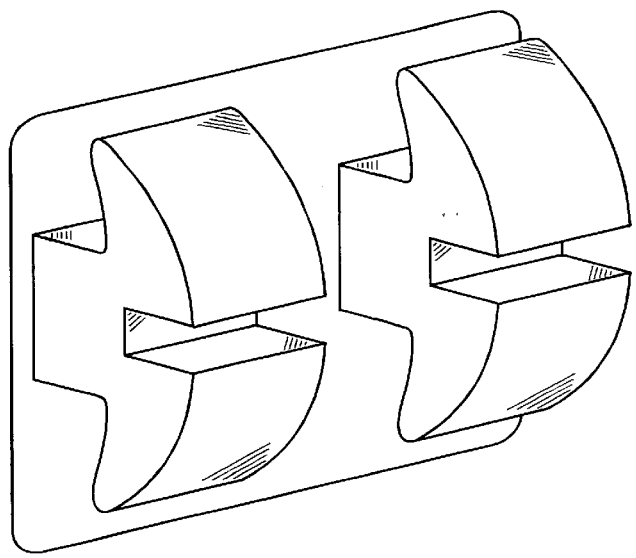
FIG. 1 is a perspective view of a typical prior art bracket known as Siamese twin edgewise bracket.
Figure 2:
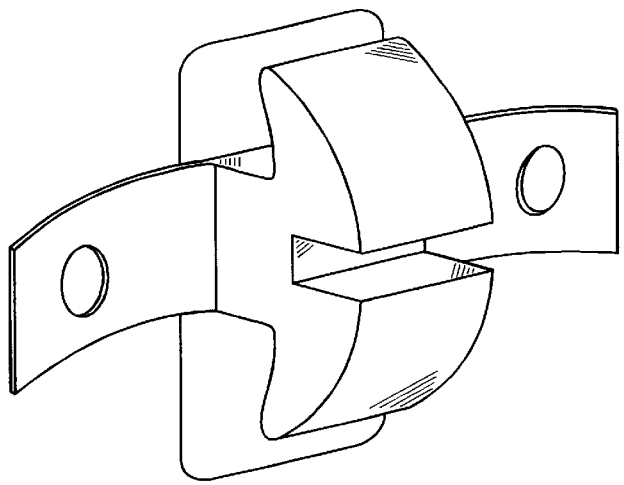
FIG. 2 is a perspective view of a typical prior art bracket showing a single edgewise bracket with rotation wings.
Figure 3:
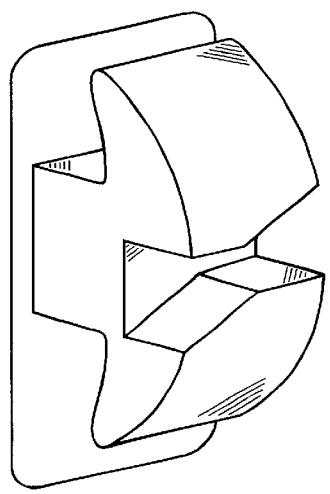
FIG. 3 is a perspective view of a bracket of prior art known as "Tip-Edge" bracket.
Figure 4A:
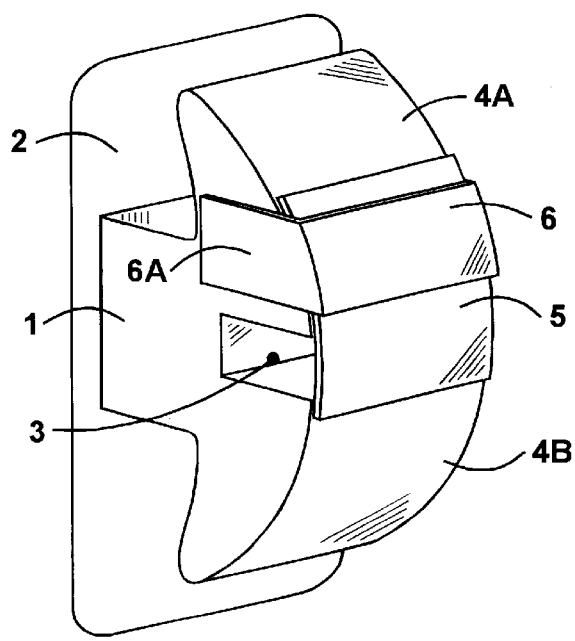
FIG. 4A is a perspective view of one embodiment of an orthodontic bracket according to the present invention showing a slidable cover in closed position, and a retainer member.
Figure 4B:
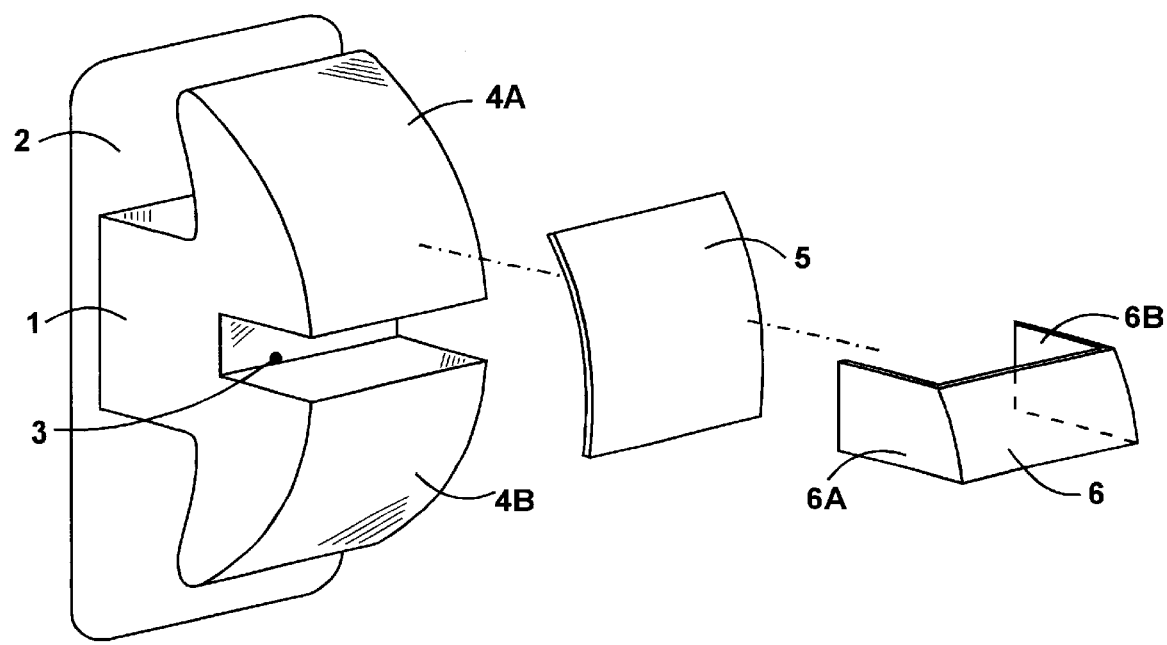
FIG. 4B is an exploded view of the bracket shown in FIG. 4A.

FIGS. 4A, 4B, 5, and 6 show a self-locking orthodontic bracket of the invention. The bracket includes a body 1 that is attached to a base 2. The body of the bracket can be of metal, plastic, ceramic or of any other permissible material. The base 2 is contoured to fit a tooth surface and can be bonded directly to a tooth or can be attached to a band material. The body 1 of the bracket has an arch wire slot 3 extending horizontally across the labial/buccal surface to engage arch wires during orthodontic treatment to exert pressure. At least one tie wing 4A projects out vertically from the body 1, which may be of a gingivally-projecting or occlusally-projecting nature. Another tie wing 4B may extend out vertically opposite to the tie wing 4A. These are used for the attachment of auxiliaries like elastic chains and ligature wires. A retainer member 6 having a transverse part and two horizontal extensions 6A and 6B at the end is attached to the sides of the tie wing 4A. Even though the cover 5 with the retainer member 6 is shown on the tie wing 4A, it may be fitted onto the tie wing 4B. The retainer member 6 may be attached to the body by brazing, welding, clamping or any other chemical, metallurgical or mechanical means or their combination. A slidable cover 5, made of a sheet contoured to fit the surface of the tie wing 4A, is retained and guided in a passageway created between the retainer member 6 and the surface of the tie wing 4A. The cover 5 and the retainer member 6 can be of any rigid substance like metal, plastic, ceramic or any other permissible material. The cover 5 is moved vertically towards the tip of the tie wing 4A to open the slot 3 and in the opposite direction to close the slot 3 after engaging an arch wire therein. FIGS. 4A and 6 show the slot 3 in closed position and FIG. 5 shows the slot 3 in open position.

Figure 9A:
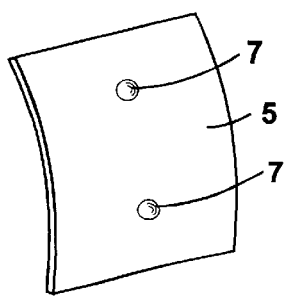
FIGS. 9A to 9H show perspective views of different embodiments of the slidable cover of the present invention.

FIG. 7 shows another embodiment of the present invention wherein the mesial and the distal ends of the tie wing 4A are joined together by a cross-member 6 to form a passageway there under, above the surface of the tie wing 4A. A slidable cover 5 is held and guided in the passageway formed between the retainer member 6 and the tie wing 4A. A small elevation 7A is formed in the retainer member 6 that makes a depression on the inner surface. The cover 5 has a pair of small elevations 7 (as shown in FIG. 9A) which corresponds to open and closed positions of the arch wire slot 3. When the cover 5 is moved into open position the elevation 7 of the cover 5 gets into the elevation 7A in the transverse retainer member 6 that is a depression on the inner surface of the retainer member thereby preventing it from sliding further and getting separated from the bracket. When the cover 5 is moved into closed position the other elevation 7 in the slidable cover 5 gets into the elevation 7A in the retainer member 6 to prevent further movement of the cover.

FIG. 8 shows another embodiment of the present invention wherein the slidable cover 5 is held on to the surface of the tie wing 4A by two sheets 6C and 6D bent at right angles. The sheets 6C and 6D are attached on to the sides of the tie wing 4A and form a channel on the surface of the tie wing 4A. The cover 5 has a hole 9 near the top edge. A pointed instrument can be inserted into the hole 9 to move the cover 5. The floor of the arch wire slot 3 has a groove 22. The bottom edge of the cover 5 gets into the groove 22 when the cover 5 is moved to close the slot 3. This would prevent the cover S from getting bent or from moving due to pressure from an arch wire held in the slot 3.

Figure 9B:
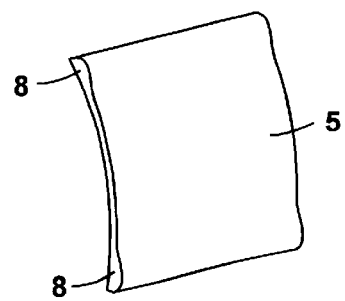
Figure 9C:
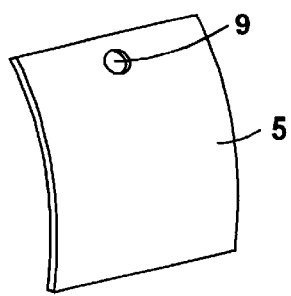
Figure 9D:
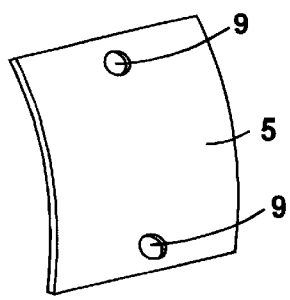
Figure 9E:
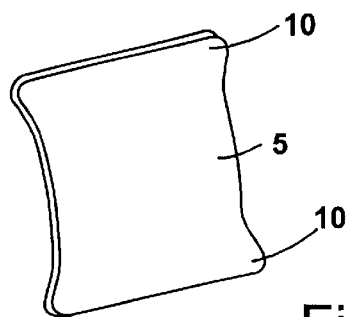
Figure 9F:
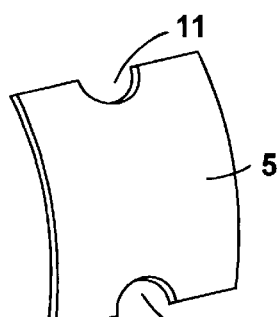
Figure 9G:
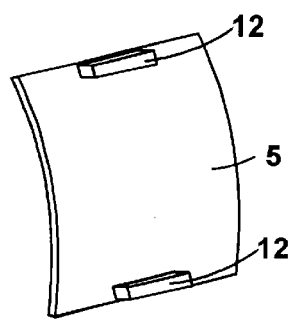
Figure 9H:
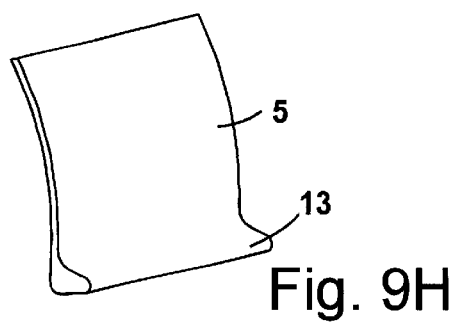

FIGS. 9A to 9H show different embodiments of the slidable cover 5 that can be used with the bracket of the invention. FIG. 9A shows two elevations 7 near the top and the bottom borders of the cover 5. These increase the fitting of the cover 5 between the retainer member 6 and the tie wing 4A thereby reducing the chances of accidental separation of the cover from the bracket. FIG. 9B shows the cover 5 with thickened top and bottom borders 8 that prevent separation of the cover 5 from the bracket. FIG. 9C shows a hole 9 near the top border of the cover 5 which can be used to move the cover 5 up and down to open and close the arch wire slot 3 by inserting a pointed instrument therein. FIG. 9D shows two holes 9 near the top and the bottom borders for the same function. FIG. 9E shows lateral extensions 10 of the vertical borders of the cover 5 near the top and the bottom borders. These extensions 10 prevent separation of the cover 5 from the bracket. FIG. 9F shows a pair of notches 11 in the top and the bottom borders of the cover 5. These can be used for opening and closing the arch wire slot 3 by engaging a pointed instrument therein. FIG. 9G shows a pair of extrusions 12 on the surface of the cover near the top and the bottom borders. These act as stops to prevent dislodgment of the cover and can be used to move the cover 5 to open and close the slot 3. FIG. 9H shows the cover 5 with a lip-like or lip shaped projection 13 formed at the border near the arch wire slot 3. The slot 3 can be opened by pressing an arch wire 14 (shown in FIGS. 10B, 18B, 18C, 29, and 30) against the lip-like projection 13.

Figure 10A:
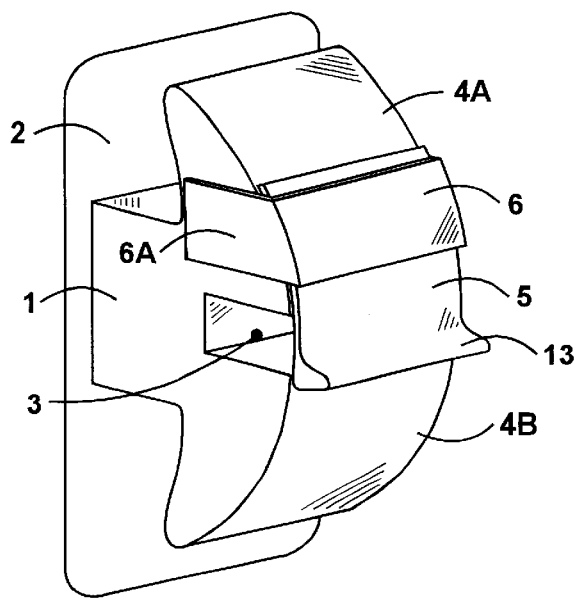
FIG. 10A is a perspective view of another embodiment of an orthodontic bracket according to the present invention.
Figure 10B:
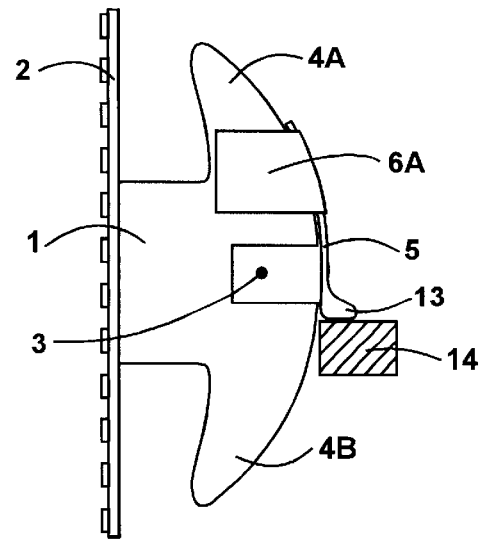
FIG. 10B is a side view of the orthodontic bracket of FIG. 10A.

FIGS. 10A and 10B show another embodiment of the present invention wherein the slidable cover 5 is having the lip-like projection 13 from the bottom border. An arch wire 14 can be pressed against the projection 13 to open the slot 3.

Figure 11A:
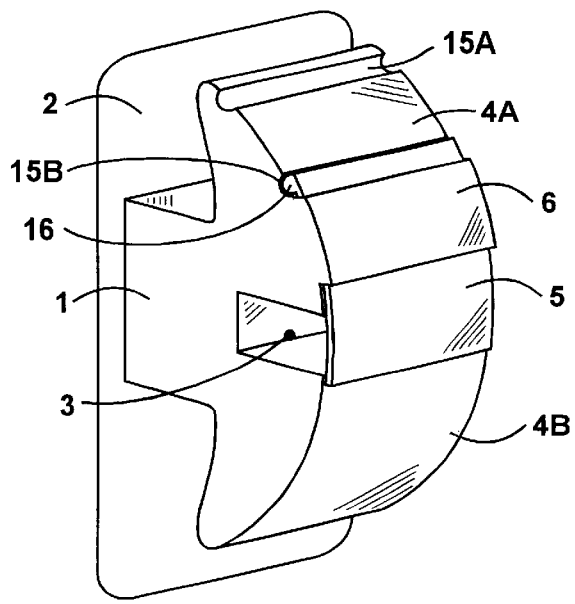
FIG. 11A is a perspective view of another embodiment of an orthodontic bracket according to the present invention.
Figure 11B:
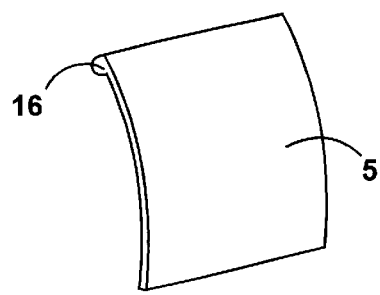
FIG. 11B is a perspective view of another embodiment of a slidable cover according to the present invention.

FIG. 11A shows a pair of grooves 15A and 15B made on the surface of the tie wing 4A. The top border of the slidable cover 5 has a semicircular thickening 16 projecting towards the tie wing. The semicircular thickening 16 gets engaged into the grooves 15A and 15B when the cover 5 is moved to open and close the arch wire slot 3 respectively. This prevents separation of the cover 5 from the bracket and holds the cover firmly over the surface of the tie wing 4A. FIG. 11B shows the cover 5 with the semicircular thickening 16 of the top border.

Figure 12:
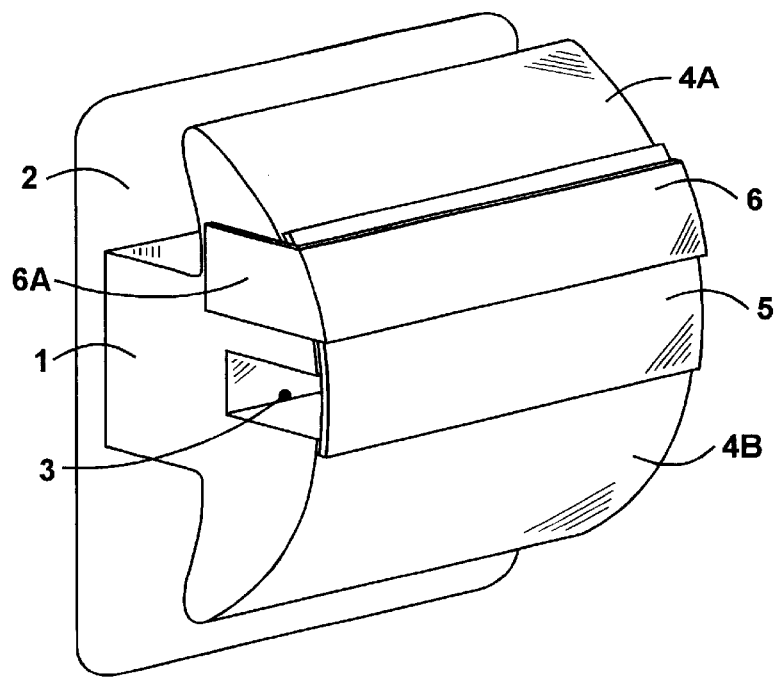
FIG. 12 is a perspective view of another embodiment of an orthodontic bracket according to the present invention.

The bracket of the invention can be wider as shown in FIG. 12. to provide better rotation control over a tooth.

Figure 13:
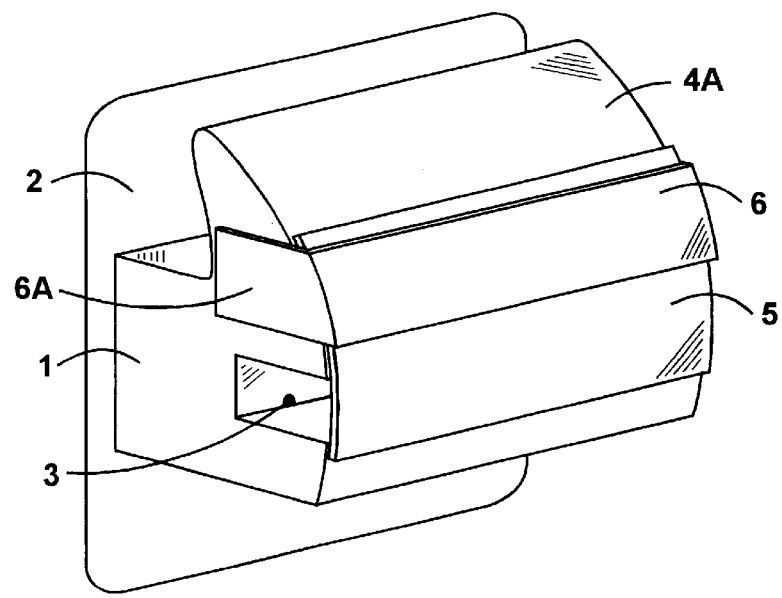
FIG. 13 is a perspective view of another embodiment of an orthodontic bracket according to the present invention.

One embodiment of the bracket has only one tie wing as shown in FIG. 13. This embodiment can be used as a molar tube. The slidable cover 5 can be opened to insert an arch wire sideways. It is easier to insert an arch wire in an open tube than in a closed tube.

Figure 14:
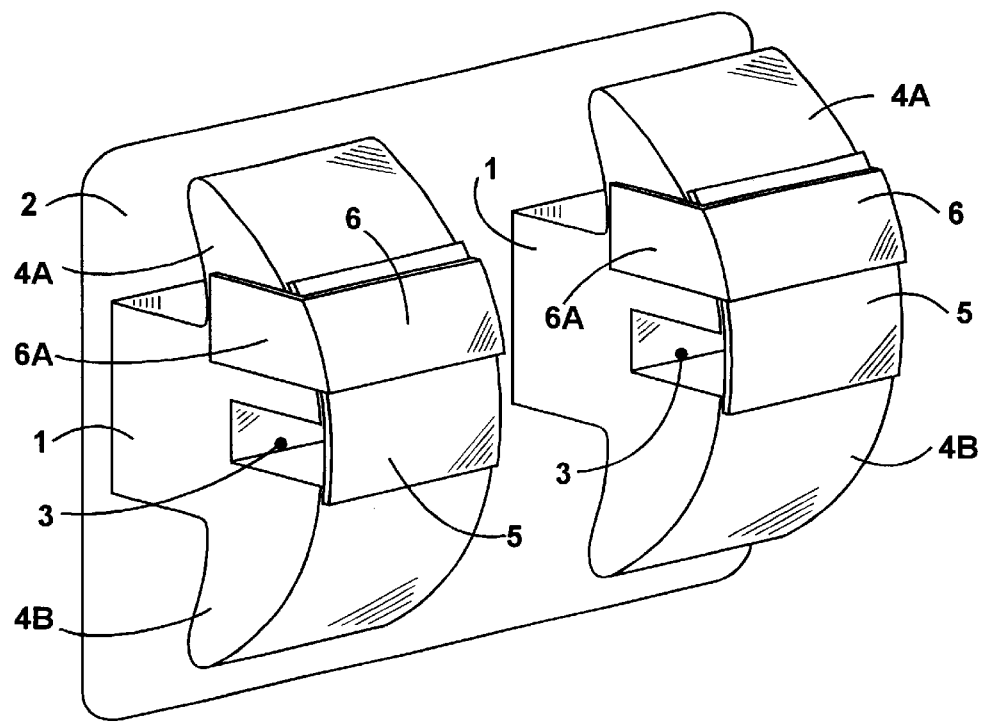
FIG. 14 is a perspective view of another embodiment of an orthodontic bracket according to the present invention.

FIG. 14 shows a pair of brackets of the invention mounted on a base to make a twin bracket to exert better rotation control.

Figure 15:
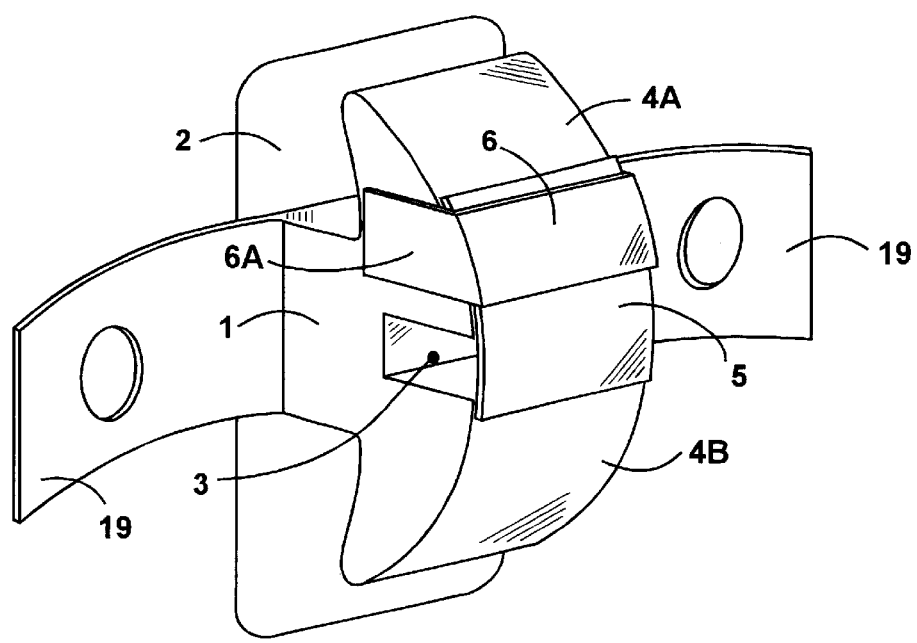
FIG. 15 is a perspective view of another embodiment of an orthodontic bracket according to the present invention.

Another embodiment of the bracket of the invention has a pair of extensions 19 on either side of the body as shown in FIG. 15 to provide better rotation control over a tooth.

FIGS. 16A and 16B show another embodiment of the present invention that has a pair of retainer arms 20A that extend horizontally from the slidable cover 5 on either side of the tie wing 4A. These extensions are bent into guide channels 21 provided on either side of the tie wing 4A. The slidable cover 5 can be moved up and down to open and close the arch wire slot 3. The guide channels retain the slidable cover 5 on the surface of the tie wing and also prevent its accidental detachment. A hole 9 is provided near the top border of the cover 5 to move it with a sharp instrument. Although the cover S is shown to be on the tie wing 4A it may be fitted over tie wing 4B instead of tie wing 4A.

The slidable cover 5 in another embodiment as shown in FIGS. 17A and 17B has a pair of extensions 20B that are bent around the tie wing 4A. The labial and the lingual surfaces of the tie wing 4A are essentially parallel to each other so that the slidable cover 5 can be moved up and down to open and close the arch wire slot. The tip of the tie wing 4A has a bulge 23 lingually to prevent separation of the slidable cover. The bulge 23 may be on the labial surface as well. Although the cover 5 is shown to be on the tie wing 4A it may be fitted over tie wing 4B instead of tie wing 4A.

In another embodiment of the present invention as shown in FIG. 18A, the slidable cover S has an extension 17 with a terminal part 18. The extension 17 extends vertically over the labial and the lingual surfaces of the tie wing 4A and over the top surface of the body 1 up to the base 2 where the terminal part 18 is attached to the body 1. The extension 17 is flexible so that when pressure is applied to the cover 5 to open the arch wire slot 3, the cover 5 moves towards the tip of the tie wing 4A. Once an arch wire is seated into the arch wire slot 3 the pressure on the cover 5 can be released and the cover 5 would automatically close the arch wire slot 3 due to the flexibility of the extension 17. The flexible extension 17 may be made, in whole or in part, of a Ti-based alloy or of a super elastic or shape memory alloy, such as a Ni-Ti-based alloy, or a Ni-Ti- Nb alloy. The cover 5 of FIG. 18A has a notch 11 in the border to be engaged by a pointed instrument. The cover 5 has a lip-like projection 13 in another embodiment as shown in FIGS. 18B and 18C. An arch wire 14 can be pressed on to the projection 13 to open the slot 3. Although the cover S is shown to extend over the tie wing 4A it may instead extend over tie wing 4B.

One more embodiment of the bracket of the invention (FIGS. 19A and 19B) has only one tie wing 4B. The slidable cover 5 is attached to a flexible extension 17 that extends over the body 1 of the bracket and an attachment part 18 that is attached to the body 1 near the base 2. The slot 3 opens when the cover 5 is pushed up and closes on removing the pressure applied to cover 5 due to the flexible extension 17.

In another embodiment of the present invention shown in FIGS. 19C and 19D, the bracket has a smaller tie wing 4A as compared to the tie wing 4B. The flexible extension 17 has a cut out portion in the middle to accommodate the tie wing 4A. The cover 5 can be moved up to open the slot 3 and the slot 3 would close automatically due to the flexible cover 17 once the pressure is removed.

Figure 20A:
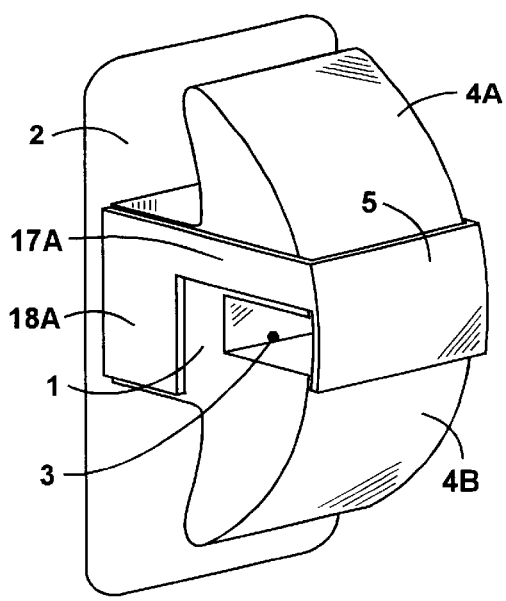
FIG. 20A is a perspective view of another embodiment of an orthodontic bracket according to the present invention showing a slidable cover in closed position.
Figure 20B:
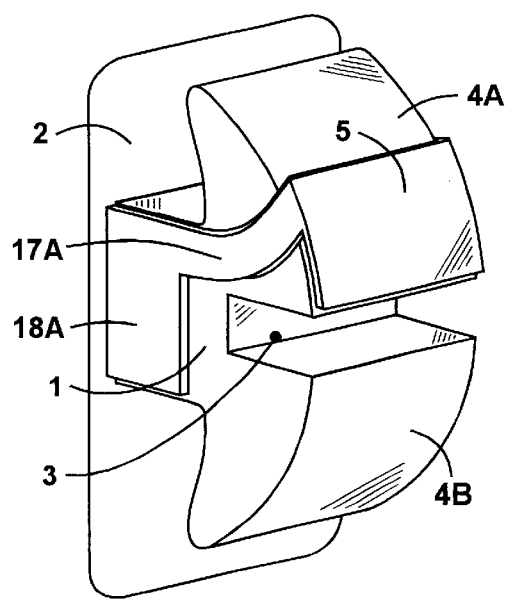
FIG. 20B is a perspective view of the orthodontic bracket of FIG. 20A showing the slidable cover in open position.

FIGS. 20A and 20B show a different embodiment of the bracket of the invention wherein the slidable cover 5 has a pair of horizontal flexible extensions 17A, and terminal parts 18A which are attached to the sides of the body 1. The horizontal extensions 17A from the slidable cover 5 bypass the arch wire slot 3 from above. The extensions 17A, which may be made of a Ti-based or of a super elastic or shape memory alloy, bend when the cover 5 is moved up to open the slot 3. As soon as the pressure to open the slot 3 is released, the cover 5 would close the slot 3 due to pressure from the bent flexible extensions 17A.

Figure 21A:
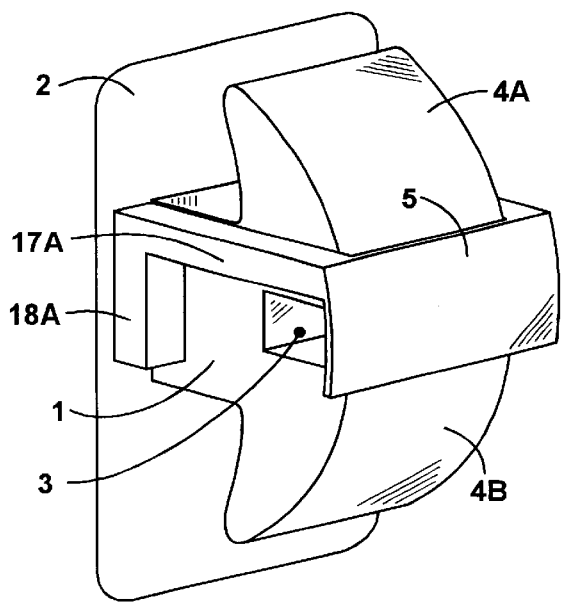
FIG. 21A is a perspective view of another embodiment of an orthodontic bracket according to the present invention showing a slidable cover in closed position.
Figure 21B:
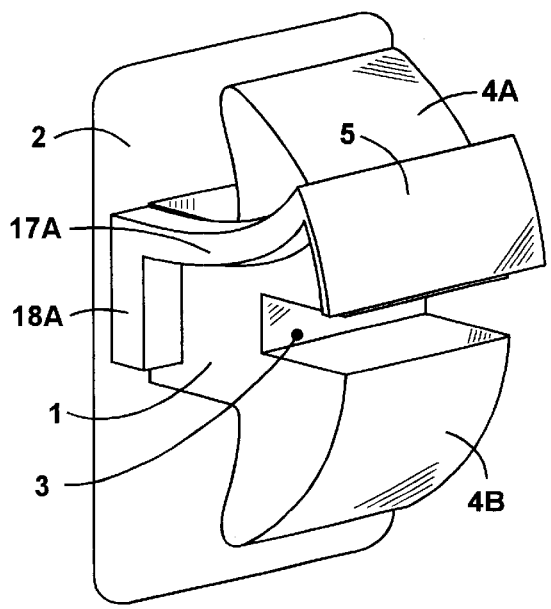
FIG. 21B is a perspective view of the orthodontic bracket of FIG. 21A showing the slidable cover in open position.

The terminal parts 18A of the slidable cover 5 may be attached to the base 2 instead of the body 1 as shown in FIGS. 21A and 21B. The cover 5 may also be wider than the bracket.

Figure 22:
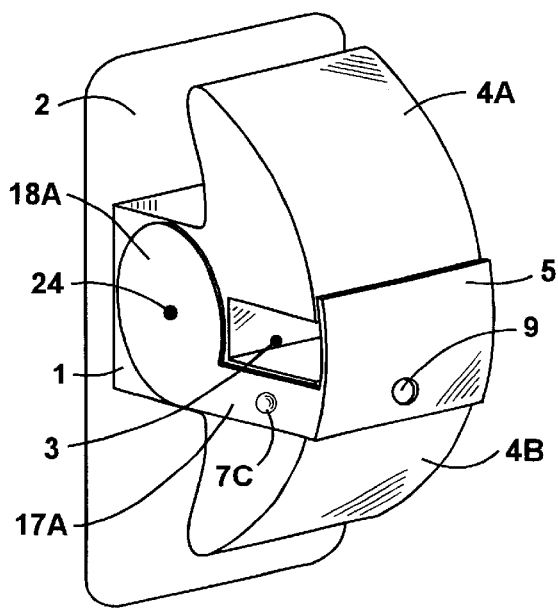
FIG. 22 is a perspective view of another embodiment of an orthodontic bracket according to the present invention showing a slidable cover in closed position.
Figure 23:
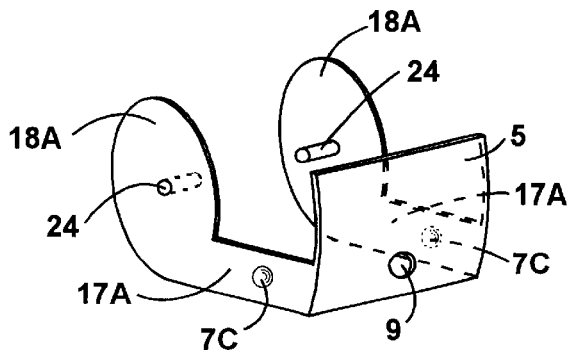
FIG. 23 is a perspective view of the slidable cover of FIG. 22.
Figure 24:
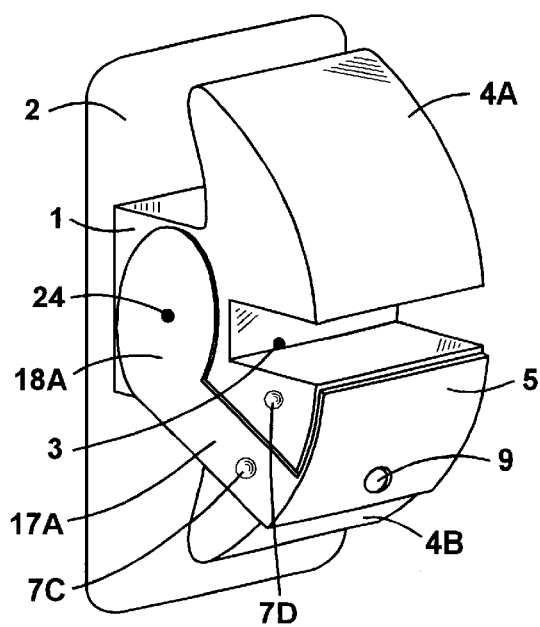
FIG. 24 is a perspective view of the orthodontic bracket of FIG. 22 showing the slidable cover in open position.

FIGS. 22, 23, and 24 show a different embodiment of the self-locking bracket of the present invention. A slidable cover 5 fits over the tie wing 4B. Even though the cover 5 is shown on the gingival tie wing 4B, it may be fitted onto the incisal tie wing 4A. The cover 5 has a pair of rigid extensions 17A projecting horizontally on either side of the body 1 bypassing the arch wire slot 3 from below. The extensions 17A are connected to terminal parts 18A which have inward projections 24 that act as pivot and are inserted into a pair of holes on the sides of the body 1 (not shown in figures). Conventional drilling methods, such as laser beam, electron beam or ion beam, or any other suitable process, may be used to form the holes. The cover 5 can be moved vertically to open and close the arch wire slot 3 around the pivot 24 and over the surface of the tie wing 4B. The cover 5 has a hole 9 near the bottom border to engage a pointed instrument for opening and closing the slot 3. The body 1 has a pair of elevations 7D on either side which correspond to a pair of elevations 7C on the extensions 17A which are depressions on the inner surface. When the cover 5 is in closed position the elevations 7D get into the elevations 7C in the extensions 17A and prevent the cover 5 from opening the slot 3. The terminal parts 18A rotate around the projections 24 when the cover 5 is moved to open and close the slot 3.

Figure 25:
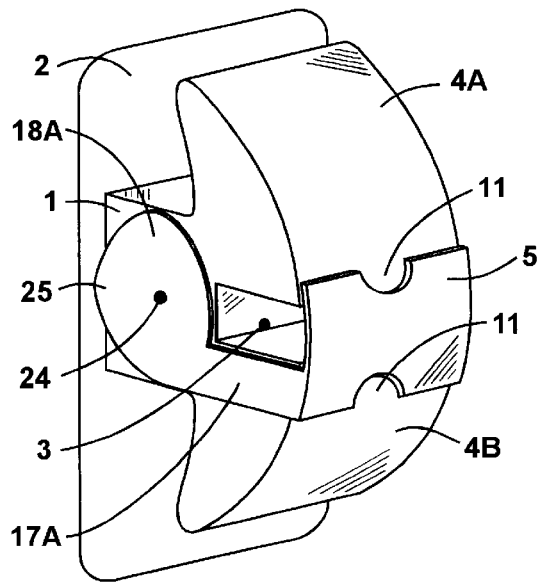
FIG. 25 is a perspective view of another embodiment of an orthodontic bracket according to the present invention showing a slidable cover in closed position.
Figure 26:
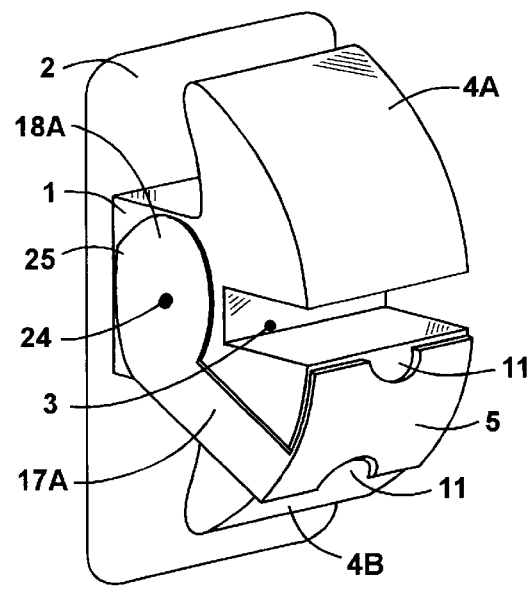
FIG. 26 is a perspective view of the orthodontic bracket of FIG. 25 showing the slidable cover in open position.

At least one of terminal parts 18A of the embodiment shown in FIGS. 25 and 26 has a pointed or triangular or cone shaped projection 25 from the border opposing the base 2. The projection 25 presses against the base 2 when the cover 5 is in closed position to prevent the cover 5 from moving towards open position. The cover has a pair of notches 11 in the top and the bottom borders.

Figure 27:
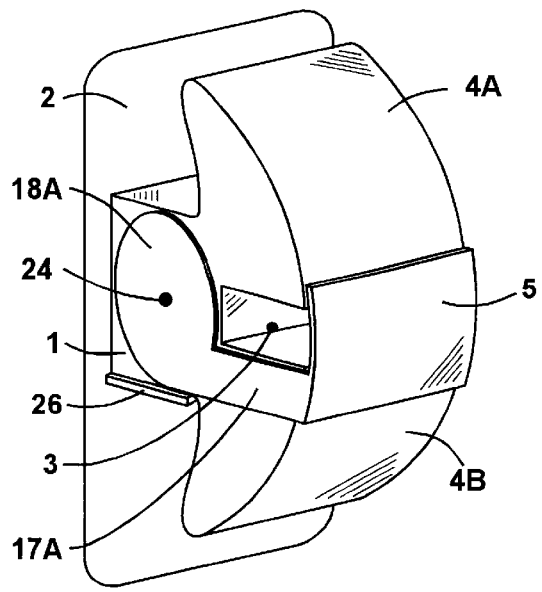
FIG. 27 is a perspective view of another embodiment of an orthodontic bracket according to the present invention showing a slidable cover in closed position.
Figure 28:
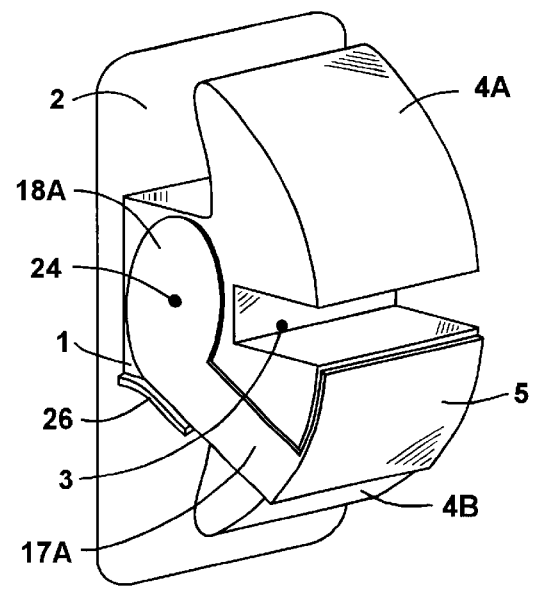
FIG. 28 is a perspective view of the orthodontic bracket of FIG. 27 showing the slidable cover in open position.

FIGS. 27 and 28 show another embodiment of the bracket of FIG. 22 with the cover in closed and open positions respectively. A flexible sheet 26 is attached to the bottom surface of the body 1 near the base 2. The other end of the sheet 2 is in contact with the bottom borders of the extensions 17A. When the cover 5 is moved to open the slot 3 the flexible sheet 26 bends. Once the pressure to open the slot 3 is removed the sheet 26 pushes the cover to close the slot 3. The sheet 26 may be made of a Ti-based alloy or of a super elastic or shape memory alloy.

Figure 29:
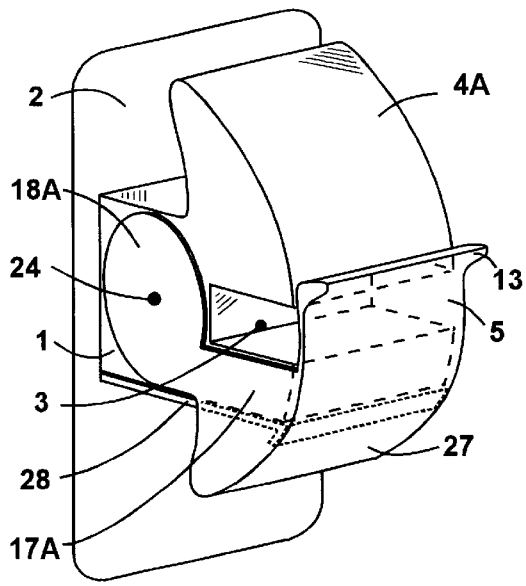
FIG. 29 is a perspective view of another embodiment of an orthodontic bracket according to the present invention showing a slidable cover in closed position.
Figure 30:
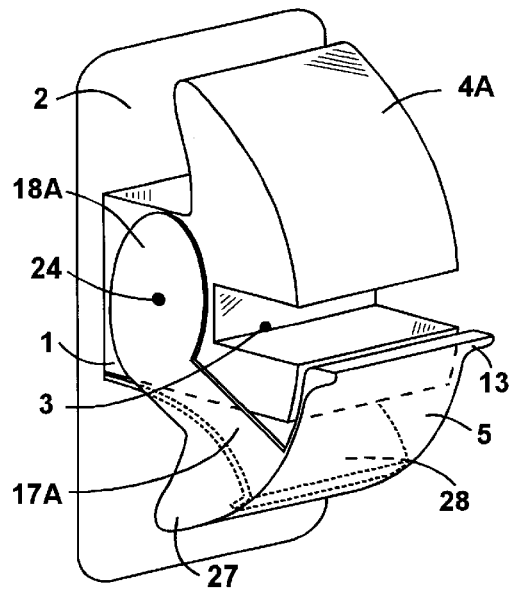
FIG. 30 is a perspective view of the orthodontic bracket of FIG. 29 showing the slidable cover in open position.
Figure 31:
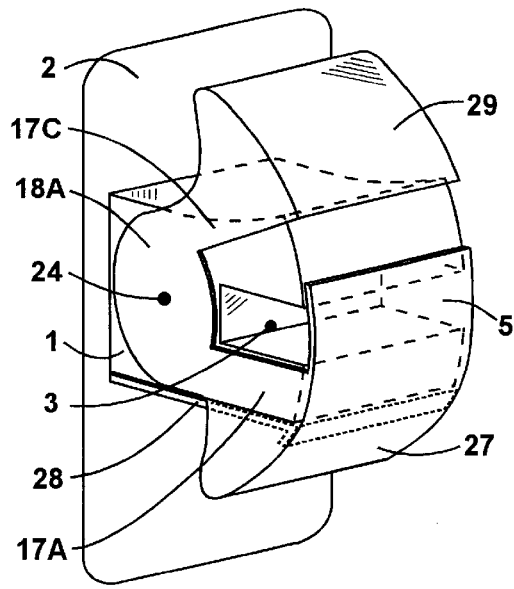
FIG. 31 is a perspective view of another embodiment of an orthodontic bracket according to the present invention showing a slidable cover in closed position.
Figure 32:
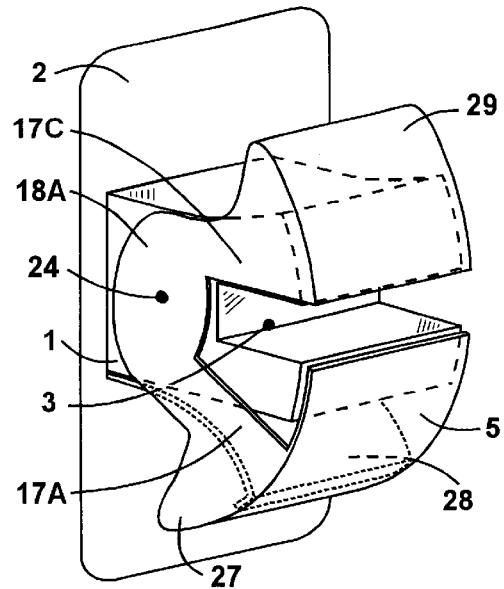
FIG. 32 is a perspective view of the orthodontic bracket of FIG. 31 showing the slidable cover in open position.

Another embodiment of the present invention as shown in FIGS. 29 and 30 has only one tie wing 4A. The slidable cover 5 has a pair of extensions 17A on either side of the body 1 with a pair of terminal parts 18A having inwards projections 24 fitted into corresponding holes in the body 1. The top border of the cover 5 has a lip-like projection 13. The bottom borders of the cover 5 and the extensions 17A project vertically down to form a tie wing 27. A flexible sheet 28 is attached to the body 1 on the lower surface near the base 2. The other end of the sheet 28 is attached to the inner surface of the tie wing 27. The cover 5 would be kept in closed position by the sheet 28. When force is applied to the cover to open the slot 3 the sheet 27 bends and forces the cover back into closed position once the pressure to open the slot 3 is removed. The sheet 28 may be made of a Ti-based or of a super elastic or shape memory alloy.

The embodiment of FIG. 29 can be changed to another embodiment (FIGS. 31 and 32) wherein the body 1 does not have tie wing 4A. Instead another tie wing 29 is formed along with the cover 5 and is attached to the terminal parts 18A by extensions 17C on either side of the body 1. The tie wing 29 is formed in such a manner that a gap is kept between the lower border of the tie wing 29 and the upper border of the cover 5. The height of the gap equals or exceeds that of the slot 3 to allow insertion and removal of an arch wire into the slot 3 without any difficulty

CONCLUSION, RAMIFICATIONS, AND SCOPE OF THE INVENTION

Although the description above contains many specificities, these should not be construed as limiting the scope of the invention but as merely providing illustrations of some of the presently preferred embodiments of this invention. For example, the bracket and the slidable cover can have various shapes like round, square, oval, triangular, rhomboid, trapezoid etc. The slidable cover may be attached to a spring to close the arch wire slot automatically instead of a flexible sheet. The different features of the slidable cover like holes, notches, elevations, thickened borders, extruded portions, depressions, lip like projections, etc. can be combined with the different embodiments of the bracket illustrated in the description of the invention.

The embodiments with extensions having pivots in the terminal portions can have holes instead of projections and the body can have projections which fit into the holes in the extensions so that the slidable cover can rotate around these projections.

Although a groove in the floor of the arch wire slot is shown in only one embodiment it can be present in all the embodiments where the slidable cover does not have a lip like projection.

The embodiments of the invention can have hooks added to the tie wings for engaging elastics.

The different embodiments described here can also have built-in force vectors (e.g., torque, and tip).

The different embodiments described here can be attached to the labial as well as the lingual surfaces of teeth. They can also be twin type brackets or single brackets with rotation wings. The slidable cover and the retainer member can be fixed on to any of the existing edgewise and modified edgewise brackets.

Although the edges of the bracket, the slidable cover and the retainer member are sharp in the drawings, they would be smoothened in the manufactured brackets to make them comfortable to the patients.

Accordingly, the scope of the invention should be determined not by the embodiments illustrated, but by the appended claims and their legal equivalents.

What is claimed is:

1. A self-locking orthodontic bracket comprising:
    a base contoured to fit a tooth surface, a body extending from said base, said body having a mesially-distally extending slot for receiving an orthodontic arch wire and a tie wing projecting out from said body;
    a slidable cover to open and close said arch wire slot by sliding over the buccal surface of said tie wing; and a transverse retainer member with a pair of extensions attached to the mesial and the distal surfaces of said body and said tie wing to retain and guide said cover in a passageway formed there under.

2. The self-locking orthodontic bracket defined in claim 1 wherein the mesiodistal width of said bracket is in the range of 1–7 mms.

3. The self-locking orthodontic bracket defined in claim 1 wherein said body includes an opposing tie wing.

4. The self-locking orthodontic bracket defined in claim 3 wherein said opposing tie wing is placed more labial; the floor of said slot has a groove to receive said cover in closed position; and said cover has a hole near the top edge to engage a pointed instrument to open and close said slot.

5. The self-locking orthodontic bracket defined in claim 3 wherein said retainer member is formed by a transverse cross member joining the ends of said tie wing thereby forming a passageway to retain said cover.

6. The self-locking orthodontic bracket defined in claim 3 wherein said retainer member is split into two parts.

7. The self-locking orthodontic bracket defined in claim 3 wherein the buccal surface of said tie wing has two spaced apart grooves extending from the mesial to the distal surface corresponding to open and closed positions of said cover; and said cover has a semicircular lingual projection on the top edge extending from side to side to act as a stop by engaging the groves on said tie wing.

8. The self-locking orthodontic bracket defined in claim 3 wherein the self-locking orthodontic bracket comprises a twin type bracket.

9. The self-locking orthodontic bracket defined in claim 3 wherein the self-locking orthodontic bracket comprises a single wing type bracket.

10. The self-locking orthodontic bracket defined in claim 3 wherein the sides near the top and the bottom edges of said slidable cover bulge outwards to limit vertical movement of said slidable cover to prevent accidental separation of said slidable cover from said bracket.

11. The self-locking orthodontic bracket defined in claim 3 wherein a means is provided to move said cover with a sharp instrument to open and close said arch wire slot.

12. The slidable cover defined in claim 11 wherein said means provided to move said cover is selected from the group consisting of a hole, a notch, and a lip-like projection.

13. The self-locking orthodontic bracket defined in claim 3 wherein the top and the bottom edges of said slidable cover are thicker than said slidable cover to provide a means for moving said slidable cover and to prevent accidental separation of said slidable cover.

14. The self-locking orthodontic bracket defined in claim 3 wherein said slidable cover has buccal projections near the top and the bottom edges to prevent accidental separation of said slidable cover from said bracket.

15. The self-locking orthodontic bracket defined in claim 3 wherein said slidable cover has a flexible extension from the top edge which extends over the buccal surface and the lingual surface of said tie wing, and over said body up to said base following the contour of said tie wing and is attached to said body near said base such that said arch wire slot can be opened by pushing the bottom edge of said slidable cover and said arch wire slot closes automatically on releasing the pressure over said slidable cover due to flexibility of said flexible extension.

16. The self-locking orthodontic bracket defined in claim 15 wherein said flexible extension from said cover is made of a material selected from the group consisting of super elastic and shape memory alloys.

17. The self-locking orthodontic bracket defined in claim 15 wherein the edge of said slidable cover near said arch wire slot has a lip-like buccal projection to allow an arch wire to push said slidable cover to open said arch wire slot.

18. A self-locking orthodontic bracket comprising:
    a base contoured to fit a tooth surface, a body extending from said base, said body having a mesially-distally extending slot for receiving an orthodontic arch wire;
    and a slidable cover for retaining an arch wire in said slot; said cover having an extension over said body and a terminal part attached to said body near sad base; said extension being flexible enough to bend when said slot is opened by sliding said cover over the buccal surface of said body.

19. The self-locking orthodontic bracket defined in claim 18 wherein said flexible extension from said cover is made of a material selected from the group consisting of super elastic and shape memory alloys.

20. The self-locking orthodontic bracket defined in claim 18 wherein said body includes a tie wing projecting from the surface opposite to said extension of said cover.

21. The self-locking orthodontic bracket defined in claim 20 wherein said extension of said cover has a cut-out portion; and said body includes a smaller tie wing projecting out through said cut-out portion of said extension.

22. A self-locking orthodontic bracket comprising:

a base contoured to fit a tooth surface, a body extending from said base, said body having a mesially-distally extending slot for receiving an orthodontic arch wire and a pair of tie wings projecting on either side of said slot;

and a slidable cover for retaining an arch wire in said slot; said cover having a pair of extensions near the top border extending on either side of one of said tie wings; said extensions bent snugly around said tie wing to retain and guide said cover on to said tie wing to open and close said slot.

23. The self-locking orthodontic bracket defined in claim 22 wherein the tip of said tie wing is thicker on the lingual surface to prevent accidental separation of said slidable cover from said bracket.

24. The self-locking orthodontic bracket defined in claim 22 wherein said tie wing has a pair of guide channels on the mesial and the distal surfaces aligned to each other and parallel to the buccal surface of said tie wing; said extensions of said slidable cover get engaged into said guide channels on said tie wing to retain and guide said cover to open and close said arch wire slot.

25. A self-locking orthodontic bracket comprising:

a base contoured to fit a tooth surface, a body extending from said base, said body having a mesially-distally extending slot for receiving an orthodontic arch wire;

and a slidable cover for retaining an arch wire in said slot; said cover having a pair of extensions on either side of said body bypassing said slot; said extensions having terminal parts attached to said body.

26. The self-locking orthodontic bracket defined in claim 25 wherein said extensions are flexible enough to bend while opening said slot.

27. The self-locking orthodontic bracket defined in claim 26 wherein said flexible extensions from said cover are made of a material selected from the group consisting of super elastic and shape memory alloys.

28. The self-locking orthodontic bracket defined in claim 26 wherein said body includes a pair of tie wings projecting on either side of said slot.

29. The self-locking orthodontic bracket defined in claim 28 wherein said terminal parts are attached, to said base.

30. The self-locking orthodontic bracket defined in claim 25 wherein said body has two opposed holes on the sides aligned along a single mesial-distal axis; and said terminal parts of said extensions have a pair of inward projections which act as pivots when engaged into said holes.

31. The self-locking orthodontic bracket defined in claim 30 wherein the shape of said terminal part is selected from the group consisting of circle, oval, square, rectangular, triangular, trapezoid and rhomboid.

32. The self-locking orthodontic bracket defined in claim 30 wherein at least one of said terminal parts has a projection abutting against said base when said cover is in closed position.

33. The self-locking orthodontic bracket defined in claim 30 wherein said body includes at least one tie wing selected from the group consisting of gingivally-projecting and occlusally-projecting tie wings.

34. The self-locking orthodontic bracket defined in claim 30 wherein said body includes two tie wings.

35. The self-locking orthodontic bracket defined in claim 30 wherein a flexible sheet extending from said base towards said cover is attached to said body near said base keeping in contact with the borders of said extensions such that said sheet bends when said cover is moved to open said slot.

36. The self-locking orthodontic bracket defined in claim 35 wherein said body includes at least one tie wing.

37. The self-locking orthodontic bracket defined in claim 35 wherein said body includes two tie wings.

38. The self-locking orthodontic bracket defined in claim 35 wherein said cover and said extensions project vertically to form a tie wing; and said flexible sheet extending from said base towards said cover is attached to said body near said base on one side and to the inner surface of said tie wing on the other side such that said sheet bends when said cover is moved to open said slot.

39. The self-locking orthodontic bracket defined in claim 38 wherein said body includes one tie wing opposite said tie wing projecting from said cover and said extensions.

40. The self-locking orthodontic bracket defined in claim 38 wherein said terminal parts have extensions which are connected by a transverse member to form a second tie wing opposing said tie wing, spaced apart from said cover to allow insertion and removal of an arch wire in said slot when said cover is moved to open said slot.

41. The self-locking orthodontic bracket defined in claim 40 wherein the tip of said second tie wing has a notch for engaging a pointed instrument to open said slot.

42. The self-locking orthodontic bracket defined in claim 40 wherein said flexible sheet is made of a material selected from the group consisting of super elastic and shape memory alloys.

* * * * *